US012746353B2

(12) United States Patent
Matheis et al.

(10) Patent No.: US 12,746,353 B2
(45) Date of Patent: Sep. 29, 2026

(54) VENTILATION ARRANGEMENT AND TREATMENT METHOD

(71) Applicant: STIMIT AG, Nidau Bern (CH)

(72) Inventors: Georg Matheis, Heilbronn (DE); Ronja Müller-Bruhn, Windisch (CH); Konstantinos Raymondos, Hannover (DE)

(73) Assignee: STIMIT AG, Nidau Bern (CH)

(*) Notice: Subject to any disclaimer, the term of this patent is extended or adjusted under 35 U.S.C. 154(b) by 1021 days.

(21) Appl. No.: 17/785,634

(22) PCT Filed: Dec. 21, 2020

(86) PCT No.: PCT/EP2020/087538
§ 371 (c)(1),
(2) Date: Jun. 15, 2022

(87) PCT Pub. No.: WO2021/123452
PCT Pub. Date: Jun. 24, 2021

(65) Prior Publication Data

US 2023/0105270 A1 Apr. 6, 2023

(30) Foreign Application Priority Data

Dec. 19, 2019 (CH) .................................... 01671/19

(51) Int. Cl.
*A61N 1/36* (2006.01)
*A61B 18/00* (2006.01)
(Continued)

(52) U.S. Cl.
CPC ....... *A61M 16/0003* (2014.02); *A61N 1/3601* (2013.01); *A61N 2/006* (2013.01); *A61B 2018/00434* (2013.01)

(58) Field of Classification Search
CPC .............. A61M 16/0003; A61M 16/00; A61M 2016/0027; A61M 2016/0036;
(Continued)

(56) References Cited

U.S. PATENT DOCUMENTS

2002/0188332 A1 12/2002 Lurie et al.
2004/0193003 A1 9/2004 Mechlenberg et al.
(Continued)

FOREIGN PATENT DOCUMENTS

GB 2587392 A 3/2021
WO 2015135933 A1 9/2015
(Continued)

OTHER PUBLICATIONS

International Search Report and Written Opinion issued Mar. 1, 2021 in Intl Appl. No. PCT/EP2020/087538.
(Continued)

*Primary Examiner* — Carrie R Dorna
*Assistant Examiner* — Joshua Daryl D Lannu
(74) *Attorney, Agent, or Firm* — MEDLER FERRO WOODHOUSE & MILLS PLLC

(57) ABSTRACT

A ventilation arrangement is disclosed that includes an induction device and a control unit. The induction device has an electro-magnetic field generator with a coil design configured to generate a spatial electro-magnetic field having a targeted shape. The control unit is in communication with the induction device and configured to control the induction device to generate the electro-magnetic field. The electro-magnetic field generator of the induction device is configured to be positioned at a human or animal patient such that, for activating a diaphragm of the patient, a Phrenic nerve of the patient is stimulatable by the spatial electro-magnetic field generated by the coil design. The control unit is connectable to a ventilation machine to receive ventilation
(Continued)

data about a ventilation of the patient. The control unit is configured to evaluate the ventilation data and to operate the induction device in accordance with the evaluated ventilation data.

19 Claims, 2 Drawing Sheets

(51) Int. Cl.
*A61M 16/00* (2006.01)
*A61N 2/00* (2006.01)
*A61N 2/02* (2006.01)

(58) Field of Classification Search
CPC ...... A61M 2205/054; A61M 2230/205; A61N 1/3601; A61N 2/006; A61N 2/002; A61N 2/02; A61N 5/022; A61N 2/004; A61B 2018/00434
See application file for complete search history.

(56) References Cited

U.S. PATENT DOCUMENTS

| | | | | |
|---|---|---|---|---|
| 2011/0046432 | A1* | 2/2011 | Simon | A61N 5/0625 607/42 |
| 2012/0016280 | A1 | 1/2012 | Alverti et al. | |
| 2015/0265833 | A1 | 9/2015 | Meyyappan et al. | |
| 2015/0367127 | A1* | 12/2015 | Meyyappan | A61M 16/026 |
| 2019/0329022 | A1 | 10/2019 | Simon et al. | |
| 2022/0362570 | A1 | 11/2022 | Pemberton | |

FOREIGN PATENT DOCUMENTS

| | | | |
|---|---|---|---|
| WO | 2019154837 | A1 | 8/2019 |
| WO | 2019154839 | A1 | 8/2019 |
| WO | 2021059250 | A1 | 4/2021 |

OTHER PUBLICATIONS

Mouchawar G. ED et al., "Stimulation of Inspiratory Motor Nerves with a Pulsed Magnetic Field," Medical and Biological Engineering and Computing, vol. 28, No. 6, Nov. 1, 1990, p. 613.

Similowski et al., "Cervical Magnetic Stimulation: A New Painless Method for Bilateral Phrenic Nerve Stimulation in Conscious Humans," Journal of Applied Physiology,vol. 67, No. 4, Oct. 1, 1989, pp. 1311-1318.

Evans et al., "Temporary transvenous diaphragm pacing. vs. standard of care for weaning from mechanical ventilation: study protocol for randomized trial," Trials Journal, https://trialsjournal.biomedcentral.com/articles/10.1186/s13063-018-3171-9, Jan. 17, 2019.

* cited by examiner

VENTILATION ARRANGEMENT AND TREATMENT METHOD

TECHNICAL FIELD

The present invention relates to a ventilation arrangement and more particularly to a method of providing a specific treatment to a human or animal patient while the patient is ventilated and particularly mechanically ventilated, e.g. by a ventilation machine.

BACKGROUND ART

In medicine, it is often required to ventilate human or animal patients for maintaining vital functions of the patient. Typically, a positive pressure mechanical ventilation approach is used for such ventilation. For example, a ventilation machine having a conduit interface to be connected to a respiratory system of the patient and an air flow generator to deliver air through the conduit interface into the respiratory system of the patient can be used for ventilation.

Even though such mechanical ventilation allows for achieving an efficient provision of air or mixtures of various gases into the respiratory system/the lungs of the patient, it generally creates a varying extent and severity of complications and damages to the lung and the whole body of the patient, particularly when ventilation lasts for an extended period of time. For example, patients mechanically ventilated generally lose a large amount of muscle mass of their breathing muscle. This is associated with limited or insufficient capability to maintain sufficient spontaneous (physiological) breathing, which may lead to dependency on mechanical ventilation due to the inability of their breathing muscles (or breathing pump) to generate sufficient tidal volume/minute volume to maintain adequate ventilation. It is known that such loss of breathing muscle can reach up to 50% within the first 1-3 days of ventilation. As a result of this ventilator induced diaphragmatic dysfunction (VIDD) patients need a period of muscle recovery and training which is known as weaning. The weaning phase can be associated with further complications including pneumonia and end in dependency on mechanical ventilation, and further deterioration of the patient's general health.

One of several indications for mechanical ventilation is respiratory failure due to acute respiratory distress syndrome (ARDS), which is associated with an inflammatory response with fluid accumulation in the alveoli as a result of inflammation. Alveoli that are not adequately ventilated as a result of mechanical ventilation may collapse and create atelectasis. They cease to contribute to gas exchange. Suboptimal pressure distribution involved with positive pressure ventilation can furthermore lead to shunt areas (areas of insufficient ventilation) while high peak airway pressures associated with mechanical ventilation lead to lung injury (ventilator induced lung injury=VILI).

It is known from respiratory muscle physiology, that 2-3 training sessions per day are effective to rebuild the diaphragm and breathing function, and compatible with the workflow both in and outside the hospital setting. It is known from spirometric trials, that a bell that rings up to 2 minutes every hour to remind the patient to perform stronger than average natural inspiratory breaths can improve patient adherence, alveolar recruitment, reduce early postoperative fever duration, reduce the need for noninvasive ventilation, length of ICU stay, and 6 month mortality in certain patients (Eltoray et al. 2019). Researchers have used inspiratory resistance training with resistance levels of less than 50% of MIP for periods of 15 to 30 minutes, 1 to 3 times a day (Sprague et al., 2003)

Critical care patients receiving invasive positive pressure ventilation, especially ARDS patients, suffer additional lung damage caused by high tidal volumes and peak pressures. It has been shown that moderate tidal volumes (3-6 ml/kg of ideal body weight), so called lung-protective ventilation improve outcomes of ARDS patients as compared with higher (6-12 ml/kg ideal body weight) tidal volumes. Diaphragm stimulation avoids positive airway pressures completely and provides physiological negative pressure ventilation thus preventing the complications of positive pressure ventilation. Adequate amounts of diaphragm activation (not too much contraction) may further reduce risk of lung damage in not-healthy lungs with some stiffness or sensitivity, e.g. ARDS lungs.

Furthermore, moderate diaphragm stimulation resulting in no or small amounts of diaphragm movement and tidal volumes may simplify application and avoid the need for synchronization to the patient's spontaneous breath and/or synchronization to mechanical ventilation.

Furthermore, positive pressure ventilation is an invasive support modality that, requires an endotracheal tube inserted into the patients trachea or in some cases and time of the treatment process even a tracheotomy. This requires sedation for some time in most cases, contributing to patient inactivation, muscle loss, and lack of self determination. Some patients may not require continuous mechanical ventilation but might be capable of spontaneous breathing from time to time. Other patients may be capable of spontaneous breathing but not to a sufficient extent (tidal volume). Such patients may require active stimulation and/or training of the "breathing pump" which may, at least temporarily, replace or assist positive pressure ventilation and/or may, at least temporarily, replace or reduce unfavourable positive pressures caused by mechanical ventilation. Even though such mechanical ventilation allows for achieving an efficient provision of air into the respiratory system and the organism of the patient, it often has more or less severe drawbacks for the patient, particularly when ventilation lasts for a comparably long period. For example, patients mechanically ventilated risk to lose essential performance of their breathing muscle. It is known that such loss of breathing muscle can be up to 50% within the first 1-3 days. As a result, such patients need a period of muscle retraining which is known as weaning. For some patients such weaning can become very long resulting in so called ventilator induced diaphragmatic dysfunction (VIDD).

Or, patients being mechanically ventilated are at a risk to develop an acute respiratory distress syndrome (ARDS) which might be a result of fluid building up in the alveoli in the lung giving rise to infections. To avoid ARDS, the alveoli would need to be more or less completely ventilated regularly. However, the positive pressure involved in mechanical ventilation can lead to occlusion of the alveoli such that ventilation can be prevented or made difficult, or shunt areas.

Furthermore, mechanical ventilation can be a heavy burden for a patient, especially when being intubated, i.e. a tube is forwarded into the respiratory system of the patient to supply air. Some patients may not need continuous mechanical ventilation but might be capable of spontaneous breathing from time to time. Or some patients may be capable of spontaneous breathing but not to a sufficient extent or sufficient deep breath. Such patient may require activation of the "breathing pump" which may, at least temporarily, replace mechanical ventilation or reduce the amount of volume/pressure applied by mechanical ventilation.

Therefore, there may be a need for a system allowing reducing the carious downsides of mechanical ventilation of a patient. Additionally, there may be a need to reduce the duration of mechanical ventilation by preventing diaphragm muscle loss and strength and/or by reducing weaning time, and assist or even replace it in certain clinical scenarios as described above allowing reducing the carious downsides of mechanical ventilation of a patient.

Disclosure of the Invention

According to the invention this need is settled by a ventilation arrangement as described in a method of providing a specific treatment to a human or animal patient, and by a ventilation arrangement as defined by the features of the independent claims. Preferred embodiments are subject of the dependent claims.

In particular, in a first aspect the invention is a ventilation arrangement comprising an induction device and a control unit. The induction device is configured to be positioned at a human or animal patient such that, for activating a diaphragm of the patient, a Phrenic nerve of the patient is stimulatable by the spatial field generated by the induction device.

The term "spatial field" as used herein relates to any field spatially spread from a source such as the induction device which spatial field is suitable to stimulate a target tissue of the patient such as a nerve or other portion of the neural system or a muscular tissue and, in particular, the Phrenic nerve of the patient. The spatial field can be an electric field, an electro-magnetic field or the like.

The targeted shape of the spatial field can be achieved by the spatial field being a locally constrained, targeted field, e.g., having a peak. It can be adapted to be active in a target area being a nerve area or tissue area that shall be activated with the spatial field (e.g. the Phrenic nerve that shall be activated), which can be for example achieved by the peak in the spatial field (focality area). The electromagnetic field can have any direction and change of intensity within the target area and the targeted shape of the local field expansion can generally be any shape of the spatial field or the time-dependent field component that allows to stimulate one or more target nerves such as the Phrenic nerves effectively while minimizing other undesired co-stimulation effects of surrounding, above-lying or close-by tissues or nerves. A peak shape is an example of such targeted shape, because it maximizes effects in a focality area and minimizes effects outside this area.

For generating the spatial field, in a preferred embodiment, the induction device has an electro-magnetic field generator with a coil design configured to generate a spatial electro-magnetic field being the spatial field having the targeted shape, and the induction device is configured to be positioned at the human or animal patient by positioning the electro-magnetic field generator of the induction device at the human or animal patient such that the Phrenic nerve of the patient is stimulatable by the spatial electro-magnetic field generated by the coil design. For example, the induction device can be embodied as any of the induction devices described in WO 2019/154837 A1, or a similar device.

The coil design described herein can be or comprise at least two coils or at least one cone shaped or otherwise curved or bulged coil, or at least one cylindrical or otherwise non-flat coil. The targeted shape of the electro-magnetic field described herein can comprise a peak formed by the spatial electro-magnetic field. The electro-magnetic field generator can also be referred to as electro-magnetic field creator.

The control unit is in communication with the induction device. For this, the control unit, e.g., can be wiredly or wirelessly coupled to the induction device such that it can transmit control signals to the induction device for operating it. The control unit further is configured to control the induction device to generate the spatial field.

The control unit further is configured to receive ventilation data about a ventilation of the patient. Thereby, receiving the ventilation data can be implemented by manually or, particularly, automatically importing the ventilation data via an appropriate interface. Preferably, the control unit is connectable to a ventilation machine to receive the ventilation data about the ventilation of the patient. Such connection can be wiredly or wirelessly be implemented by an appropriate interface structure. By being connected, the control unit can receive the ventilation data in run-time which allows for efficient and sophisticated control of the induction device.

Ventilation data in this context refers to any ventilation data of the patient independent from the origin of ventilation. Such ventilation data may be induced by a mechanical ventilator or a non-invasive ventilation device or via spontaneous breath of the patient or via stimulation of breathing via the phrenic nerve. Ventilation data may be data that contains information both on ventilation intensity (e.g. diaphragm contraction intensity, tidal volume, flow velocity) as well as ventilation timing (i.e. inspiration and/or expiration detection via flow sensor/abdominal belt/etc.). Ventilation data can be acquired via flow or pressure sensors from a mechanical ventilator, or via independent flow or pressure sensors, or via a thoracic or abdominal belt equipped with strain gauges and/or accelerometers, EMG, myogram based sensors or via other diaphragm activation detection sensors.

The control unit further is configured to evaluate the ventilation data and to operate the induction device in accordance with the evaluated ventilation data.

In general, the control unit can be any computing entity suitable for performing the tasks involved for controlling the induction device and for evaluating the ventilation data and/or feedback signals and/or ventilator-independent respiratory parameter feedback. It can be or comprise a laptop computer, a desktop computer, a server computer, a tablet, a smartphone or the like. The term "control unit" covers single devices as well as combined devices. The control unit can, for example, be a distributed system, such as a cloud solution, performing different tasks at different locations.

Typically, control units or computers involve a processor or central processing unit (CPU), a permanent data storage having a recording media such as a hard disk, a flash memory or the like, a random access memory (RAM), a read only memory (ROM), a communication adapter such as an universal serial bus (USB) adapter, a local area network (LAN) adapter, a wireless LAN (WLAN) adapter, a Bluetooth adapter or the like, and a physical user interface such as a keyboard, a mouse, a touch screen, a screen, a microphone, a speaker or the like. Control units or computers can be embodied with a broad variety of components.

The control unit can be partially or fully embodied as separate component, or as a component integrated in any other device or component of the ventilation arrangement. For example, the control unit or parts of it can be embodied in the ventilation machine used for ventilating the patient, and/or in the induction device.

The control unit of the ventilation arrangement can communicate with a feedback device, designed to non-invasively monitor direct and indirect respiratory parameters independent from a ventilation machine. The control unit is designed to have the option to adapt control parameters based on a computational evaluation of said feedback.

Operating the induction device can particularly involve inducing the induction device to apply the spatial field and, thereby, stimulating the Phrenic nerve or both Phrenic nerves of the patient. Thus, the control unit can activate the diaphragm of the patient by operating the induction device.

The ventilation arrangement according to the invention allows for assisting, at least partially replacing or augmenting the ventilation provided by the ventilation machine, i.e. mechanical ventilation. Thereby, by evaluating the ventilation data and operating the induction device in accordance with the evaluated ventilation data, it can be achieved that, depending on the needs of the patient's specific clinical situation, an appropriate operation protocol and, thus, treatment can be provided. Such typically patient specific protocols may differ or may be specific in duration and repetition rate of operating the induction device. Like this, the ventilation arrangement according to the invention allows for reducing at least some of the mentioned downsides of sole mechanical or positive pressure ventilation of the patient of the prior art.

For example, diaphragm atrophy by muscle training stimuli without the necessity of providing tidal volume in the presence of a positive pressure ventilator and/or by enhancing positive pressure machine breaths with additional negative pressure tidal volumes to reduce stress and strain to the alveoli by reducing tidal volume, peak positive pressure etc. can be prevented or significantly reduced.

Preferably, the ventilation arrangement comprises a ventilation machine having a conduit interface configured to be connected to the respiratory system of the patient, an air flow generator configured to deliver air through the conduit interface into the respiratory system of the patient, and an interface unit configured to provide the ventilation data. The ventilation machine can be, e.g., a conventional or semi-conventional ventilation machine for mechanical ventilation by forwarding air into the respiratory system. By including the ventilation machine in the ventilation arrangement an efficient and sophisticated interaction between control unit and ventilation machine or a sensor that delivers oxygenation/ventilation data can be achieved. This allows for an efficient and reliable ventilation.

Preferably, the control unit is configured to operate the induction device for a stimulation duration matched to a specific treatment of the patient.

The term "stimulation duration" in this context relates to a period of time during which stimulation is performed or the Phrenic nerve is stimulated. Thereby, stimulation duration may include a continuous provision of the spatial field or, preferably, a provision of the spatial field in pulses. Each pulse may be characterized by a varying magnetic or electric or electro-magnetic field, advantageously a sine pulse of 150 microseconds (μs) to 300 μs pulse duration. Advantageously, the stimulation is performed in trains of pulses of the spatial field. Advantageously, such trains of pulses are applied in a frequency of 10 Hz to 30 Hz. Preferably, such trains of pulses are interrupted by breaks in which no pulses are applied. The trains may have a train duration and the pulses may be configured in consideration of an efficient stimulation to achieve a specific intensity or duration of diaphragm contraction or intensity or duration of inspiration. Advantageously, trains of pulses are followed by a break with no stimulation to allow diaphragm relaxation and/or expiration. For example, the trains may be configured to have varying pulse durations and/or varying pulse field intensities. The "stimulation duration" may include both continuous application of trains of pulses or trains of pulses interrupted by breaks of 1 seconds (s) to 12 s.

For example, a train may be a sequence of pulses at about 15-30 Hz which produces an inspiration or diaphragm contraction. The train duration is typically about 1 s to 1.3 s, and usually in a range of 0.5 s to 2 s, typically synchronized with the inspiration phase of the patient and/or ventilation machine. The break between the train duration is typically about 1 s to 3 s, and usually in the range of 1 s to 12 s. In the non-stimulated breaks, the patient can, e.g., expire. The impulses of such trains may be applied at constant intensity or at varying intensity, preferably at least at the beginning of the train the intensity increases (ramp protocol). The stimulation duration refers to the overall duration over which such therapeutic diaphragm stimulations are repeated. Within each stimulation duration, therapeutic diaphragm stimulations could be applied regularly (e.g., each breath or each second breath or more) or irregularly (e.g., triggered by the user).

The specific treatment to which the stimulation is matched may be a treatment involved in a therapy of the patient by ventilation. The therapy typically is adapted to the disease or impairment of the patient. Thereby, the specific treatment may be provided for a treatment duration including all stimulations provided for the stimulation durations.

By matching the stimulation duration matching the specific treatment, the ventilation arrangement can be adjusted to distinctively treat the patient in accordance with his needs for the involved therapy.

Alternatively or additionally, the control unit preferably is configured to operate the induction device at a repetition rate matched to a or the specific treatment of the patient. Like this, the specific treatment may be provided for stimulation repetition adapted to the specific treatment which allow for increasing the efficiency of the therapy.

Thereby, the control unit preferably is configured to define the stimulation duration and/or to define the repetition rate.

Such definition can be implemented by providing a user interface allowing a practitioner to set specific values and particularly the stimulation duration and/or repetition. For example, the control unit can provide a user interface such as a graphical user interface (GUI) by which the practitioner can input appropriate values, i.e., like fixed rate and volume ventilation for example. Defining the stimulation duration and repetition rate can also be implemented by preconfiguring the control unit such that it is set for one or more specific combinations of duration and repetition rates. Thereby, for example, the control unit can provide a selection of appropriate combinations of durations and repetition rates suitable to provide specific treatments. Furthermore, defining the duration and repetition rate can be implemented by the control unit determining the stimulation duration and the repetition rate via an evaluation of the ventilation data. For example, the control unit can be embodied or programmed to recognize a specific problem or need when evaluating the data obtained by the ventilation machine and to determine the stimulation duration and repetition rate in accordance with the recognized problem or need. Or, the user could input a specific patient problem or need via the user interface.

By allowing to define the stimulation duration and/or the repetition rate, the control unit can efficiently be configured to the specific treatment. In particular, the ventilation arrangement can be customized for various specific treatments as desired in the therapy of the patient.

In the following, various preferred configurations of the ventilation arrangement according to the invention are described which allow to apply specific treatment. In particular, the ventilation arrangement can be specifically configured for one or plural specific treatments as follows.

In a first preferred embodiment, the specific treatment is prevention of diaphragm muscle loss and/or reduction of risk of ventilator induced diaphragmatic dysfunction, wherein the repetition rate is in a range of about once per day to about 3 times per day or more, and wherein the stimulation duration is in a range of about 3 minutes to about 20 minutes. The stimulation duration may also be in a range of about 11 minutes to about 30 minutes or even more. By such combinations of stimulation duration and repetition rate, muscle loss can efficiently be prevented and/or the risk of ventilator induced diaphragmatic dysfunction (VIDD) can efficiently and essentially reduced.

In a second preferred embodiment, the specific treatment is reduction of risk of developing an acute respiratory distress syndrome or ventilator associated pneumonia or ventilator-induced lung injury or atelectasis. Thereby, the repetition rate preferably is in a range of about twice per hour to about every two hours, and wherein the stimulation duration is in a range of about 0.5 minutes to about 3 minutes. Alternatively, the stimulation duration preferably is in a range of about 1 breathing cycle to about 5 breathing cycles. Thereby, the repetition rate preferably is in a range of about every minute to about every 30 minutes. This protocol could be interrupted during night times, e.g. if necessary for intensive care unit (ICU) workflow.

Such configuration of the stimulation duration and repetition rate according the second preferred embodiment allows for efficiently promoting ventilation of the alveoli or opening of the alveoli or favorable pressure creation in the alveoli and/or for improving the therapy of an acute respiratory distress syndrome (ARDS) and by reducing time on positive pressure ventilation the incidence of ventilator associated pneumonia (VAP) may be reduced and ventilator-induced lung injury (VILI) may be mitigated. In particular, activating the diaphragm to a sufficient extent allows ventilating the alveoli via physiological, negative pressure rather than or in combination with positive pressure ventilation.

In a third preferred embodiment, the specific treatment is prevention, delay or replacement of ventilation or reduction of high positive pressures during mechanical ventilation, wherein repetition rate is at every spontaneous breath of the patient. Thereby, the stimulation duration preferably is continuously 24 hours a day. Such configuration allows for reducing or eliminating the downsides of mechanical ventilation.

In general, the term “spontaneous breath” as used herein relates to a breath induced by the patient himself and, particularly not induced by the induction device. Thereby, a breath typically includes a combination of typically one inhalation and typically one exhalation. It also may include breaks where neither inhalation nor exhalation occurs.

In a fourth preferred embodiment, the specific treatment is prevention, delay or replacement of ventilation or reduction of high positive pressures during mechanical ventilation, and wherein repetition rate is, during night time, at every spontaneous breath of the patient, and, during day time, not operating the induction device.

The terms “night time” and “day time” used in this connection may relate to a time frame in which the patient mainly is awake (day time) or asleep (night time). For example, the night time may be defined to be between 22.00 and 07.00 and the day time vice versa or the like.

In a fifth preferred embodiment, the control unit is configured to operate the induction device to induce breathing cycles in the patient or to induce intermittent deep breath in the patient. Like this, the mechanical ventilation can be assisted or, in certain cases, at least for a given time, completely replaced.

The operation of the induction device in accordance with the fourth preferred embodiment can be applied when necessary. For finding out, when such operation is necessary, the ventilation arrangement my involve an oxygen or carbon dioxide level measured in the blood of the patient. Thereby, such measurement may be provided by any means but, preferably, the ventilation arrangement comprises a sensor unit to sense the oxygen level in the blood of the patient or a carbon dioxide level in the blood of the patient, wherein the control unit is in communication with the sensor unit, and the control unit is configured to operate the induction device when sensed oxygen level or the sensed carbon dioxide level bypasses a predefined threshold. Like this, assistance or replacement of the mechanical ventilation provided by the ventilation machine by activation of the diaphragm via the induction device can be achieved in an automatic fashion. This allows for providing a safe and efficient appropriate ventilation or treatment.

The control unit can be provided to implement any single one or any combination of the first to fourth preferred embodiments mentioned above.

Preferably, the ventilation data comprises a tidal breath of the patient. The term “tidal breath” as used herein may relate to a flow or air flow generated by breathing. Thereby, the tidal breath typically involves a positive flow such as generated by exhalation and a negative flow such as generated by inhalation.

The tidal breath involved in the ventilation data can be gathered by any suitable means such as a flow sensor included in the ventilation machine. However, preferably, the ventilation arrangement comprises a tidal breath sensor to sense the tidal breath of the patient, wherein the control unit is in communication with the tidal breath sensor. Such tidal breath sensor comprised by the ventilation arrangement itself allows for accurately and efficiently obtaining and evaluating the required information.

Thereby, in a first preferred variant, the control unit is configured to adjust a field intensity and a train duration of the induction device such that the tidal breath is in a range of about 3 ml per kg body weight to about 6 ml per kg body weight. Such comparably weak breaths may be particularly efficient when treating ARDS.

In a second preferred variant, the control unit is configured to adjust a field intensity and a train duration of the induction device such that the patient produces a tidal breath in a range of about 6 ml per kg body weight to about 8 ml per kg body weight. Such breaths may be particularly beneficial for training the patient.

In a third preferred variant, the control unit is configured to adjust a field intensity and a train duration of the induction device such that the patient produces a tidal breath in a range of about 0 ml per kg body weight to about 3 ml per kg body weight. Such weak breaths may be particularly advatageous to synchronize the patient with the ventilation machine which, e.g., may increase acceptance of the mechanical ventilation.

In a fourth variant, the control unit is configured to adjust a field intensity of the induction device such that the patient produces deep and strong breaths in a range of about 9 ml per kg body weight to about 15 ml per kg body weight. Like this, so called deep breaths can be induced which can be beneficial for various reasons in plural treatment.

Preferably, wherein the control unit is configured to re-adjust operation of the induction device in accordance with tidal breath of the patient. Such repetitive auto adjustment allows for ensuring providing appropriate treatment over time.

Preferably, the ventilation data comprises a diaphragm contraction of the patient. Evaluating diaphragm contraction allows of involving direct information about the effect of the induced stimulation.

Thereby, the ventilation arrangement preferably comprises a diaphragm contraction sensor to sense the diaphragm contraction of the patient, wherein the control unit is in communication with the diaphragm contraction sensor.

The control unit preferably is configured to re-adjust operation of the induction device in accordance with diaphragm contraction of the patient.

Preferably, the control unit is configured to operate the induction device such that trains of the generated spatial field are provided. In particular, such trains may be trains of pulses of the spatial field as described in more detail below. The trains may be provided consecutively, wherein they may be interrupted by breaks. Provision of trains allows for inducing an efficient stimulation.

Thereby, each train preferably comprises an increase of an intensity of the spatial field ending at a target intensity of the spatial field. Such increase resulting in a ramp protocol allows for increasing acceptance of the stimulation as an acute reaction of the body of the patient caused by sudden comparably high intensity can be prevented. Also, the sum of the intensities of consecutive trains may be increased.

In a second aspect, the invention is a method of providing a specific treatment to a human or animal patient being ventilated. The method comprises the steps of: obtaining an induction device configured to generate a spatial field having a targeted shape, positioning the induction device at a human or animal patient, and operating the induction device to stimulate a Phrenic nerve of the patient by the spatial field generated by the induction such that the diaphragm of the patient is activated.

As mentioned above, ventilation of the patient can be provided by a ventilation machine forwarding air into the respiratory system of the patient. Thereby, it can be particularly advantageous to implement the method of the second aspect of the invention and/or to apply the any of the ventilation arrangements of the first and third aspects of the invention soon after, at the same time or even before starting ventilation by means of the ventilation machine. In particular, it may be beneficial to start stimulation from day one of the mechanical ventilation, e.g., in an intensive care unit (ICU). Like this, it can be prevented that excessive defatigation of the breathing muscles and particularly the diaphragm occurs. Atrophy of the muscle tissue can, thus, be prevented.

In connection with the present invention, the term "ventilation" relates to any type of creating tidal breath. It may involve negative pressure ventilation such as, similarly to spontaneous breathing, is induced by stimulating the diaphragm, positive pressure ventilation as induced by mechanical ventilation forwarding air into the respiratory system, or non-invasive ventilation such as ventilation by minor positive pressure. In cases where the lung tissue or the alveoli are impaired, positive pressure ventilation may damage the lung such that in many cases mechanical ventilation may be disadvantageous, at least when not combined with other measures.

The method according to the invention and its preferred embodiments described below, allows to efficiently implement the effects and benefits of the ventilation arrangement and its preferred embodiments described above. Thereby, the method can be implemented by using a ventilation arrangement as described above or by any other suitable structure. In particular, the method according to the invention allows for implementing the specific treatments described above and below.

Preferably, the induction device used in the method has an electro-magnetic field generator with a coil design to generate a spatial electro-magnetic field as the spatial field having the targeted shape, wherein the electro-magnetic field generator of the induction device is positioned at a human or animal patient, and wherein the induction device is operated to stimulate the Phrenic nerve of the patient by the spatial electro-magnetic field generated by the coil design.

Operating the induction device to stimulate the Phrenic nerve of the patient preferably comprises operating the induction device for a stimulation duration matched to the specific treatment. Thereby, the method preferably comprises a step of defining the stimulation duration in accordance with the specific treatment.

Alternatively, or additionally operating the induction device to stimulate the Phrenic nerve of the patient preferably comprises repeatedly operating the induction device at a repetition rate matched to the specific treatment. Thereby, the method preferably comprises a step of defining the repetition rate in accordance with the specific treatment.

In a first preferred embodiment of the method according to the invention, the specific treatment is prevention of diaphragm muscle loss and/or reduction of risk of ventilator induced diaphragmatic dysfunction (VIDD), wherein the repetition rate is in a range of about once per day to about 3 times per day, and wherein the stimulation duration is in a range of about 3 minutes to about 20 minutes. The stimulation duration may also be in a range of about 11 minutes to about 30 minutes or even more.

In a second preferred embodiment of the method according to the invention, the specific treatment is reduction of risk of developing an ARDS, VAP or VILI or the prevention of alveoli closure, and the induction device is repeatedly operated in regular intervals throughout the day. Thereby, the induction device either preferably is repeatedly operated at a repetition rate in a range of about twice per hour to about every two hours for a stimulation duration in a range of about 0.5 minutes to about 3 minutes. Or, the induction device preferably is repeatedly operated for a stimulation duration in a range of about 1 breathing cycle to about 5 breathing cycles, wherein the induction device preferably is repeatedly operated at a repetition rate in a range of about every minute to about every 30 minutes.

In a third preferred embodiment of the method according to the invention, the specific treatment is keeping or rebuilding function of the respiratory center which is connected to the phrenic nerve.

In a fourth preferred embodiment of the method according to the invention, the specific treatment is induction of breathing cycles or stimulation of deep breathing, comprising measuring an oxygen level or a carbon dioxide level in the blood of the patient, wherein operating the induction device when the measured oxygen level or carbon dioxide level bypasses a predefined threshold.

In a fifth preferred embodiment of the method according to the invention, the specific treatment is prevention, delay or replacement of ventilation or reduction of high positive pressures during mechanical ventilation, wherein repetition rate is at every spontaneous breath of the patient.

Thereby, the fifth embodiment of the method according to the invention preferably is implemented in the following two variants.

In a first variant, the stimulation duration is continuously 24 hours a day.

In a second variant, the repetition rate is, during night time, at every spontaneous breath of the patient, and, during day time, not operating the induction device.

In both variants, the induction device preferably is operated to stimulate the Phrenic nerve of the patient superimposed in a target rhythm not being synchronous with spontaneous breath of the patient. The term "superimposed" in this connection related to stimulation in addition to spontaneous and/or ventilation machine induced breathing. For example, such stimulation allows for guiding the breathing of the patient.

Preferably, a field intensity and a train duration of the induction device are adjusted such that the patient produces a tidal breath in a range of about 3 ml per kg body weight to about 6 ml per kg body weight.

Preferably, a field intensity and a train duration of the induction device are adjusted such that the patient produces a tidal breath in a range of about 6 ml per kg body weight to about 8 ml per kg body weight.

Preferably, a field intensity and a train duration of the induction device are adjusted such that the patient produces a tidal breath in a range of about 0 ml per kg body weight to about 3 ml per kg body weight.

Preferably, a field intensity of the induction device is adjusted such that the patient produces deep and strong breaths in a range of about 9 ml per kg body weight to about 15 ml per kg body weight.

Preferably, the method according to the invention is implemented by a ventilation arrangement according to the invention.

Preferably, operating the induction device comprises providing trains of the generated spatial field. Thereby, each train preferably comprises an increase of an intensity of the spatial field ending at a target intensity of the spatial field.

In a third aspect, the invention is a ventilation arrangement comprising an induction device configured to generate a spatial field having a targeted shape, and a control unit in communication with the induction device and configured to control the induction device to generate the spatial field. The control unit and the induction device can be identically or similarly embodied as described above in connection with the first aspect of the invention. In particular, the electro-magnetic field generator of the induction device is configured to be positioned at a human or animal patient such that, for activating a diaphragm of the patient, a Phrenic nerve of the patient is stimulatable by the spatial field generated by the induction device. Furthermore, the control unit is configured to operate the induction device to induce a breathing cycle in the patient or to induce a deep breath in the patient.

The third aspect of the invention allows for achieving at least some of the effects and benefits described above in connection with the first aspect of the invention or its preferred embodiments. In particular, ventilation of the patient can be assisted or, in certain cases, at least for a given time, completely replaced, without requiring any mechanical ventilation. Thus, in accordance with the third aspect of the invention, it is not necessary to evaluate ventilation data obtained by a ventilation machine, but ventilation of the patient can be directly assisted by means of stimulation.

In the following preferred embodiments of the ventilation of the third aspect of the invention are defined which, particularly, allow to achieve the effects and benefits described above in connection with the first and second aspects of the invention.

Preferably, the induction device has an electro-magnetic field generator with a coil design configured to generate a spatial electro-magnetic field being the spatial field having the targeted shape, and wherein the induction device is configured to be positioned at the human or animal patient by positioning the electro-magnetic field generator of the induction device at the human or animal patient such that the Phrenic nerve of the patient is stimulatable by the spatial electro-magnetic field generated by the coil design.

The ventilation arrangement preferably comprises a sensor unit to sense an oxygen level in the blood of the patient or a carbon dioxide level in the blood of the patient, wherein the control unit is in communication with or connectable to the sensor unit, and the control unit is configured to operate the induction device when sensed oxygen level or the sensed carbon dioxide level bypasses a predefined threshold. This sensor unit can be used for efficiently and automatically finding out, when operation of the induction device is necessary. Like this, assistance of the patient's ventilation by activation of the diaphragm via the induction device can be achieved in an automatic fashion. This allows for providing a safe and efficient appropriate ventilation or treatment.

Preferably, the control unit is connectable to a ventilation machine to receive ventilation data about a ventilation of the patient, and the control unit is configured to evaluate the ventilation data and to operate the induction device in accordance with the evaluated ventilation data.

Thereby, the ventilation arrangement preferably comprises a ventilation machine having a conduit interface configured to be connected to the respiratory system of the patient, an air flow generator configured to deliver air through the conduit interface into the respiratory system of the patient, and an interface unit configured to provide the ventilation data.

Preferably, the control unit is configured to define a stimulation duration matched to a specific treatment of the patient and/or a repetition rate matched to the specific treatment of the patient, and to operate the induction device in accordance with the defined stimulation duration and/or the determined repetition rate or based on the patient's breathing pattern per strain gauge or other sensors measuring the respiratory cycle. Thereby, the control unit preferably is configured to define the stimulation duration and/or the repetition rate.

Preferably, the specific treatment is prevention of diaphragm muscle loss and/or reduction of risk of ventilator induced diaphragmatic dysfunction, wherein the repetition rate is in a range of about once per day to about 3 times per day, and the stimulation duration is in a range of about 3 minutes to about 20 minutes. The stimulation duration may also be in a range of about 11 minutes to about 30 minutes or even more.

Preferably, the specific treatment is reduction of risk of developing an acute respiratory distress syndrome or ventilator associated pneumonia or ventilator induced lung injury or atelectasis, wherein the repetition rate is in a range of about twice per hour to about every two hours, and the stimulation duration is in a range of about 0.5 minutes to about 3 minutes.

Preferably, the specific treatment is reduction of risk of developing an acute respiratory distress syndrome or ventilator associated pneumonia or ventilator-induced lung injury or atelectasis, and the stimulation duration is in a range of about 1 breathing cycle to about 5 breathing cycles.

Thereby, the repetition rate preferably is in a range of about every minute to about every 30 minutes.

Preferably, the specific treatment is prevention, delay or replacement of ventilation or reduction of high positive pressures during mechanical ventilation, and the repetition rate is at every spontaneous breath of the patient.

Thereby, the stimulation duration is continuously 24 hours a day.

Preferably, the specific treatment is prevention, delay or replacement of ventilation or reduction of high positive pressures during mechanical ventilation, and wherein repetition rate is, during night time, at every spontaneous breath of the patient, and, during day time, not operating the induction device.

Preferably, the ventilation arrangement comprises a tidal breath sensor to sense the tidal breath of the patient, wherein the control unit is in communication with the tidal breath sensor.

Thereby, the control unit preferably is configured to adjust a field intensity and a train duration of the induction device such that the tidal breath is in a range of about 3 ml per kg body weight to about 6 ml per kg body weight.

Additionally or alternatively, the control unit preferably is configured to adjust a field intensity and a train duration of the induction device such that the patient produces a tidal breath in a range of about 6 ml per kg body weight to about 8 ml per kg body weight.

The control unit preferably is configured to adjust a field intensity and a train duration of the induction device such that the patient produces a tidal breath in a range of about 0 ml per kg body weight to about 3 ml per kg body weight.

The control unit preferably is configured to adjust a field intensity of the induction device such that the patient produces deep and strong breaths in a range of about 9 ml per kg body weight to about 15 ml per kg body weight.

Preferably, the control unit is configured to re-adjust operation of the induction device in accordance with tidal breath of the patient.

Preferably, the ventilation arrangement comprises a diaphragm contraction sensor to sense the diaphragm contraction of the patient, wherein the control unit is in communication with the diaphragm contraction sensor.

Thereby, the control unit preferably is configured to re-adjust operation of the induction device in accordance with diaphragm contraction of the patient.

Preferably, the control unit is configured to operate the induction device such that trains of the generated spatial field are provided. Thereby, each train preferably comprises an increase of an intensity of the spatial field ending at a target intensity of the spatial field

BRIEF DESCRIPTION OF THE DRAWINGS

The ventilation arrangement and the method according to the invention are described in more detail herein below by way of exemplary embodiments and with reference to the attached drawing, in which.

DESCRIPTION OF EMBODIMENTS

Figure 1:
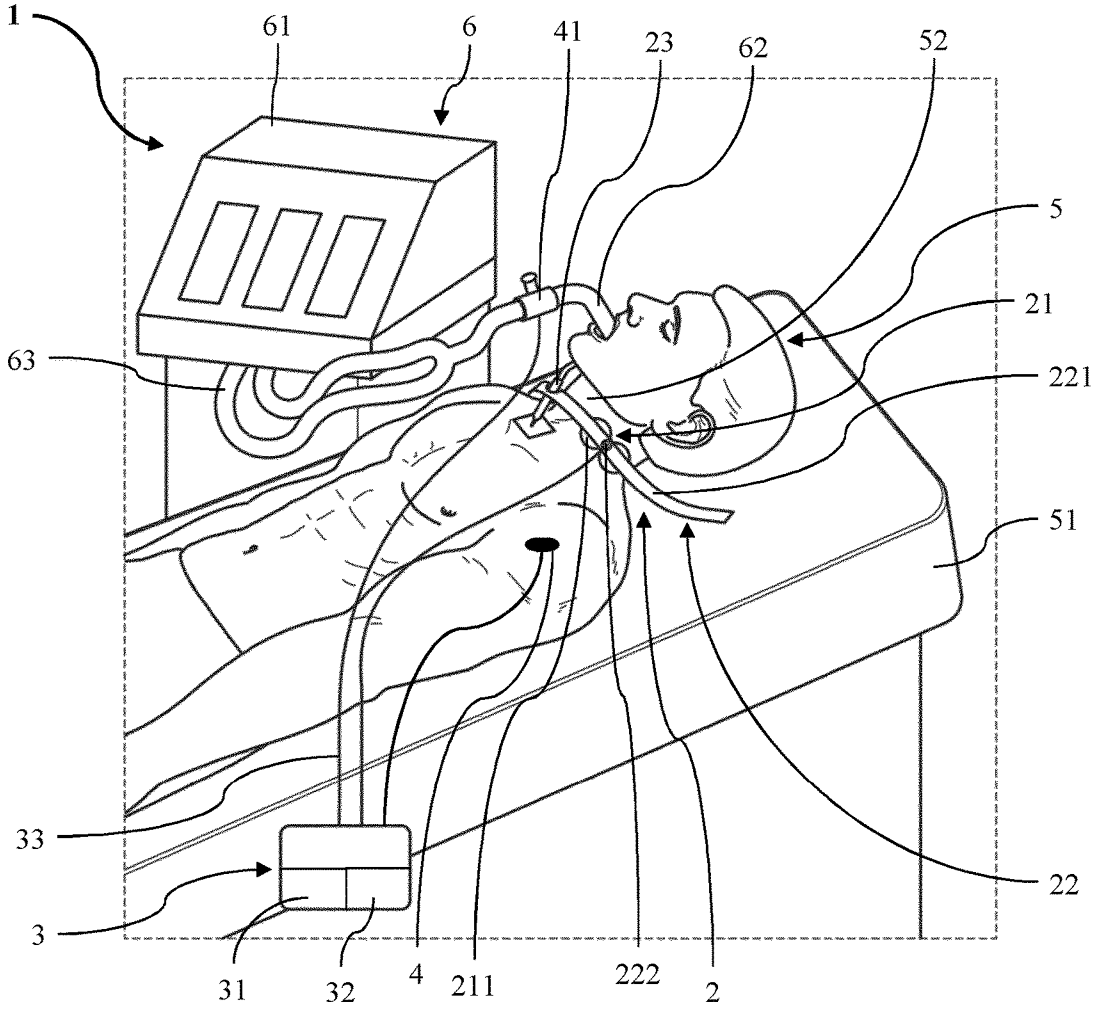
FIG. 1 shows a schematic view of an embodiment of a ventilation arrangement according to the invention implementing an embodiment of a method according to the invention.

FIG. 1 shows an embodiment of a ventilation arrangement 1 according to the invention, i.e. according to the first and third aspects of the invention. The ventilation arrangement 1 includes a ventilation machine 6, an electro-magnetic induction device 2 (in the following also referred to as EMI device), a processing unit 3 and a sensor unit 4 having an oxygen or carbon dioxide sensor. The EMI device 2 comprises an electro-magnetic field generator 21 with two coils 211 as coil design. The coils 211 are located in one common plane and configured to generate a spatial electro-magnetic field 212. When operated, the two coils 211 generate the electro-magnetic field towards a neck 52 of a patient 5. The electro-magnetic field has a central targeted shape with a focality area at which the electro-magnetic field maximally extends into the neck 52. Further, the EMI device 2 has a mounting arrangement 22 with a neck arc 221 arranged at the neck 52 of the patient 5 and fixed to a bed 51 the patient 5 lies on. The neck arc 221 is equipped with a joint 222 as repositioning structure of an electro-magnetic field adjustment mechanism of the EMI device 2. The joint 222 holds the coils 211 at the neck 52 of the patient 5.

The ventilation machine 6 comprises a ventilator 61 as air flow generator from which ventilation tubes 63 extend, and a mouthpiece 62 as conduit interface. The mouthpiece 62 is a tube provided through a mouth of the patient into the respiratory system of the patient 5.

The control unit 3 has a user interface 31 for exchanging information with a practitioner supervising or setting up ventilation of the patient 5. For example, the user interface 31 can be embodied as touch screen allowing to in- and output information. Further, the control unit 3 is equipped with a device interface 32 arranged to be coupled to an interface unit of the ventilation machine 6, the EMI device 2 and the sensor unit 4 by wires 33. Like this, the control unit 3 is in communication with the ventilation machine 6, the EMI device 2 and the sensor unit 4.

More specifically, the control unit is configured to receive ventilation data about the ventilation of the patient 5 from the ventilation machine 6 and to control the EMI device 2 to generate the electro-magnetic field in accordance with the evaluated ventilation data as described in more detail below. Furthermore, the control unit is configured to manipulate the joint 222 to automatically vary the position of the focality area 213 of the electro-magnetic field 212 generated by the coils 211 and to vary the field strength of the electro-magnetic field 212. The aim of varying field strength and position of the electro-magnetic field 212 is to adjust the electro-magnetic field 212 such that it specifically stimulates a Phrenic nerve of the patient 5. Upon stimulation of the Phrenic nerve 53, a diaphragm of the patient 5 is activated. Thereby, an airflow or breathing is induced.

The ventilation machine 6 is configured to mechanically ventilate the patient 5 by advancing air through the mouthpiece 62 into the respiratory system of the patient 5. More specifically, the ventilator 61 is configured to deliver the air through the mouthpiece 62. The control unit 3 is configured to control the ventilator 61 to deliver the air according to a breathing scheme defined in the control unit 3. Moreover, the control unit 3 regulates the activation of the diaphragm in coordination with the breathing scheme such that activation of the diaphragm via the Phrenic nerve 53 is coordinated with the ventilation of the patient 5.

For being able to provide various treatments during ventilation, the control unit 3 is configured to define combinations of a stimulation duration and a repetition rate, and to operate the EMI device 2 in accordance with the defined stimulation duration and the determined repetition rate. Thereby, the control unit 3 provides a selection of treatments to the practitioner via the user interface 31. The practitioner selects an appropriate treatment and sets parameters involved.

For allowing prevention of diaphragm muscle loss and/or reduction of risk of VIDD, a first operation mode is set in the control unit 3 by defining the stimulation duration to be in a range of about 3 minutes to about 20 minutes and the repetition rate to be in a range of about once per day to about 3 times per day.

For allowing reduction of a risk of developing an ARDS, a second operation mode is set in the control unit 3 by defining the repetition rate to be in a range of about twice per hour to about every two hours and the stimulation duration to be in a range of about 0.5 minutes to about 3 minutes.

For alternatively allowing reduction of the risk of developing ARDS, a third operation mode is set in the control unit 3 by defining the stimulation duration to be in a range of about 1 breathing cycle to about 5 breathing cycles and the repetition rate to be in a range of about every minute to about every 30 minutes.

For inducing breathing cycles or stimulating deep breathing, a fourth operation mode is set in the control unit 3. In this fourth operation mode, the control unit 3 evaluates an oxygen level or a carbon dioxide level in the blood of the patient 5 measured by the oxygen or carbon dioxide sensor of the sensor unit 4 and compares it to a predefined threshold. The control unit 3 then operates the EMI device 2 when the measured oxygen level or carbon dioxide level bypasses the predefined threshold. In particular, it operates the EMI device 2 when the measured oxygen level is below the threshold or when the measured carbon dioxide level is above the threshold.

The sensor unit 4, further comprises a tidal breath sensor and a diaphragm contraction sensor. The control unit is configured to evaluate signals provided by the tidal breath sensor and the diaphragm sensor as needed in a specific therapy.

Figure 2:
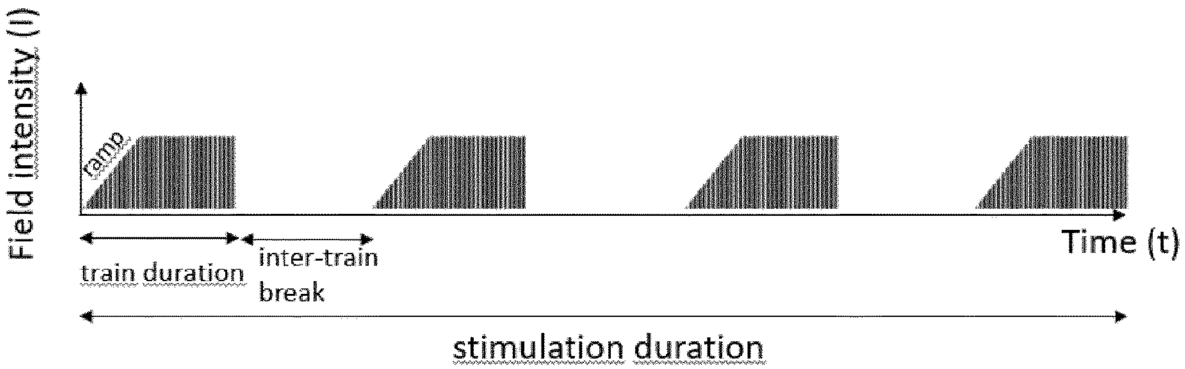
FIG. 2 shows a graph of a spatial field over time generated by an embodiment of a ventilation arrangement according to the invention in accordance with an embodiment of a method according to the invention.

In FIG. 2 generation of a spatial field by operating an induction device of an embodiment of the ventilation arrangement according to the invention or by applying an embodiment of the method according to the invention is illustrated. In particular, the generated spatial field is intended to advantageously stimulating the Phrenic nerves of a patient for activating the diaphragm of the patient.

In the graph of FIG. 2, the abscissa represents time t and the ordinate represents intensity I of the spatial field generated by the induction device. As can be seen, the spatial field is provided by plural consecutive trains T of plural pulses P. Each pulse is characterized by a varying electro-magnetic field such as a sine pulse of 200 μs pulse duration.

The intensity I of the plurality of pulses P of one single train T increases from a low initial intensity $I_0$ to a target intensity $I_t$. Once the target intensity is reached, no further increase occurs. Like this, each train is provided with a ramp R of intensity I of the spatial field. Further, each train T of the plurality of trains has an identical train duration $d_T$. Between each two following trains T an inter-train break $B_{it}$ is provided, in which no spatial field is generated. During a stimulation duration ds, the trains T are regularly provided one after the other intermitted the inter-train breaks $B_{it}$.

Figure 3:
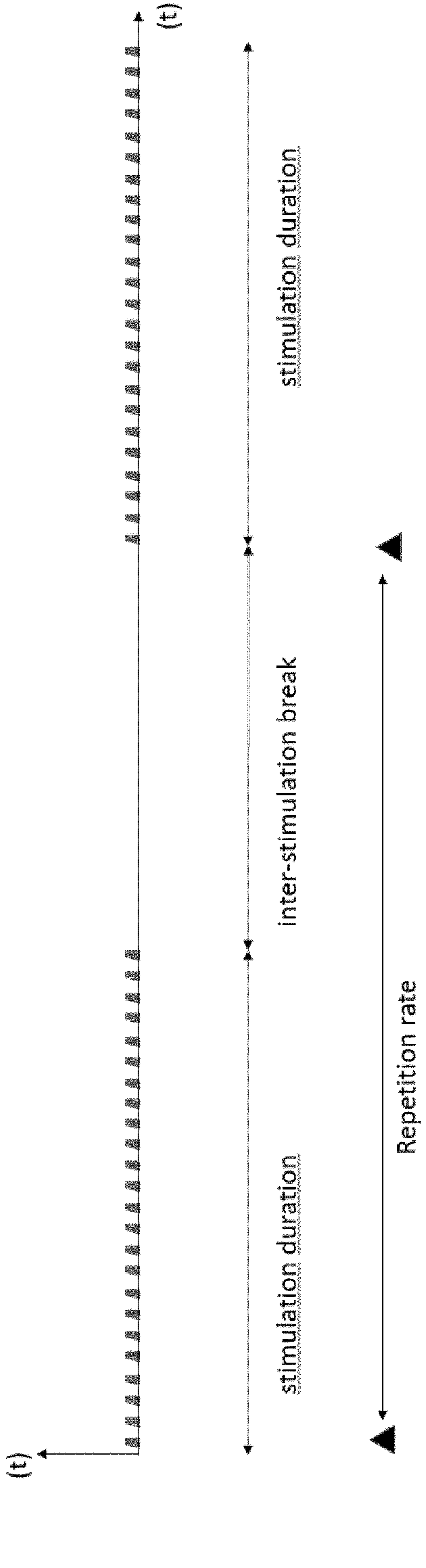
FIG. 3 shows a graph of the spatial field generation of FIG. 2 in a wider time frame.

FIG. 3 shows the generation of the spatial field of FIG. 2 on a wider scale. Thereby, it can be seen that plural consecutive stimulations as depicted in FIG. 2 are provided. In particular, each stimulation provided for the stimulation duration ds is followed by an inter-stimulation break $b_{is}$ such that each two following stimulations are intermitted by one inter-stimulation break $b_{is}$. Each one stimulation over the stimulation duration $d_S$ and its following inter-stimulation break $b_{is}$ together form a repetition rate r, which is, e.g., 15 Hz.

The stimulation protocol shown in FIG. 2 and FIG. 3 allows for inducing contraction of the diaphragm of the patient during each train T such that inhalation by the patient results. During the inter-train beaks Bit the diaphragm is relaxed such that exhalation by the patient results. The train duration $d_T$ is about 0.5 s to 2 s and is synchronized with the breathing of the patient and/or a ventilation machine. The duration of the inter-train breaks $B_{it}$ is, e.g., in the range of 1 s to 12 s.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the FIGS. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A ventilation arrangement comprising:

an induction device configured to generate a spatial field having a targeted shape; and a controller in communication with the induction device and configured to control the induction device to generate the spatial field, wherein the induction device is configured to be positioned at a human or animal patient such that, for activating a diaphragm of the patient, a Phrenic nerve of the patient is stimulable by the spatial field generated by the induction device, wherein the controller is configured to:

receive ventilation data about a ventilation of the patient, by being connectable to a ventilation machine to receive the ventilation data about the ventilation of the patient, evaluate the ventilation data and to operate the induction device in accordance with the evaluated ventilation data, and operate the induction device at a repetition rate matched to a specific treatment of the patient, wherein the controller is configured to define the repetition rate, and wherein the specific treatment is:

prevention of diaphragm muscle loss and/or reduction of risk of ventilator induced diaphragmatic dysfunction, wherein the repetition rate is in a range of about once per day to about 3 times per day, and wherein the stimulation duration is in a range of about 3 minutes to about 20 minutes, reduction of risk of developing an acute respiratory distress syndrome or ventilator associated pneumonia or ventilator induced lung injury or atelectasis, wherein the repetition rate is in a range of about twice per hour to about every two hours, and wherein the stimulation duration is in a range of about 0.5 minutes to about 3 minutes, reduction of risk of developing an acute respiratory distress syndrome or ventilator associated pneumonia or ventilator-induced lung injury or atelectasis, and wherein the stimulation duration is in a range of about 1 breathing cycle to about 5 breathing cycles, wherein the repetition rate is in a range of about every minute to about every 30 minutes, prevention, delay or replacement of ventilation or reduction of high positive pressures during mechanical ventilation, and wherein the repetition rate is at every spontaneous breath of the patient, wherein the stimulation duration is continuously 24 hours a day, or prevention, delay or replacement of ventilation or reduction of high positive pressures during mechanical ventilation, and wherein the repetition rate is, during night time, at every spontaneous breath of the patient, and, during day time, not operating the induction device.

2. The ventilation arrangement of claim 1, wherein the induction device has an electro-magnetic field generator with a coil design configured to generate a spatial electromagnetic field being the spatial field having the targeted shape, and wherein the induction device is configured to be positioned at the human or animal patient by positioning the electro-magnetic field generator of the induction device at the human or animal patient such that the Phrenic nerve of the patient is stimulable by the spatial electromagnetic field generated by the coil design.

3. The ventilation arrangement of claim 1, further comprising:

a ventilation machine having a conduit interface configured to be connected to the respiratory system of the patient;

an air flow generator configured to deliver air through the conduit interface into the respiratory system of the patient; and an interface unit configured to provide the ventilation data.

4. The ventilation arrangement of claim 1, wherein the controller is configured to operate the induction device for a stimulation duration matched to a specific treatment of the patient, wherein the controller is configured to define the stimulation duration.

5. The ventilation arrangement of claim 1, wherein the controller is configured to operate the induction device to induce a breathing cycle in the patient or to induce a deep breath in the patient, wherein the ventilation arrangement comprises a sensor unit to sense a blood oxygen level of the patient or a blood carbon dioxide level of the patient, the controller being in communication with the sensor unit, and the controller being configured to operate the induction device when sensed oxygen level or the sensed carbon dioxide level bypasses a predefined threshold.

6. The ventilation arrangement of claim 1, wherein the ventilation data comprises a tidal breath of the patient, wherein the ventilation arrangement comprises a tidal breath sensor to sense the tidal breath of the patient, the controller being in communication with the tidal breath sensor.

7. The ventilation arrangement of claim 6, wherein the controller is configured to:

adjust a field intensity and a train duration of the induction device such that the tidal breath is in a range of about 3 ml per kg body weight to about 6 ml per kg body weight, adjust a field intensity and a train duration of the induction device such that the patient produces a tidal breath in a range of about 6 ml per kg body weight to about 8 ml per kg body weight, adjust a field intensity and a train duration of the induction device such that the patient produces a tidal breath in a range of about 0 ml per kg body weight to about 3 ml per kg body weight, or adjust a field intensity of the induction device such that the patient produces deep and strong breaths in a range of about 9 ml per kg body weight to about 15 ml per kg body weight.

8. The ventilation arrangement of claim 6, wherein the control unit is configured to re-adjust operation of the induction device in accordance with the tidal breath of the patient.

9. The ventilation arrangement of claim 1, wherein the ventilation data comprises a diaphragm contraction of the patient, wherein the ventilation arrangement comprises a diaphragm contraction sensor to sense the diaphragm contraction of the patient, the controller being in communication with the diaphragm contraction sensor, and wherein the controller is configured to re-adjust operation of the induction device in accordance with diaphragm contraction of the patient.

10. A ventilation arrangement comprising:

an induction device configured to generate a spatial field having a targeted shape; and a controller in communication with the induction device and configured to control the induction device to generate the spatial field, wherein the induction device is configured to be positioned at a human or animal patient such that, for activating a diaphragm of the patient, a Phrenic nerve of the patient is stimulable by the spatial field generated by the induction device, the controller is configured to receive ventilation data about a ventilation of the patient, by being connectable to a ventilation machine to receive the ventilation data about the ventilation of the patient, and the controller is configured to evaluate the ventilation data and to operate the induction device in accordance with the evaluated ventilation data, wherein the controller is configured to operate the induction device such that trains of the generated spatial field are provided, and wherein each train comprises an increase of an intensity of the spatial field ending at a target intensity of the spatial field.

11. A method of providing a specific treatment to a human or animal patient, comprising:

obtaining an induction device configured to generate a spatial field having a targeted shape;

positioning the induction device at a human or animal patient; and operating the induction device to stimulate a Phrenic nerve of the patient by the spatial field such that a diaphragm of the patient is activated, wherein operating the induction device to stimulate the Phrenic nerve of the patient comprises repeatedly operating the induction device at a repetition rate matched to the specific treatment, comprising a step of defining the repetition rate in accordance with the specific treatment, and wherein the specific treatment is:

prevention of diaphragm muscle loss and/or reduction of risk of ventilator induced diaphragmatic dysfunction, wherein the repetition rate is in a range of about once per day to about 3 times per day, and wherein the stimulation duration is in a range of about 3 minutes to about 20 minutes, reduction of risk of developing an acute respiratory distress syndrome or ventilator associated pneumonia or ventilator-induced lung injury or atelectasis, wherein the repetition rate is in a range of about twice per hour to about every two hours, and wherein the stimulation duration is in a range of about 0.5 minutes to about 3 minutes, reduction of risk of developing an acute respiratory distress syndrome or ventilator associated pneumonia or ventilator-induced lung injury or atelectasis, wherein the stimulation duration is in a range of about 1 breathing cycle to about 5 breathing cycles, and wherein the repetition rate is in a range of about every minute to about every 30 minutes, prevention, delay or replacement of ventilation or reduction of high positive pressures during mechanical ventilation, wherein the repetition rate is at every spontaneous breath of the patient, wherein the stimulation duration is continuously 24 hours a day, and wherein the induction device is operated to stimulate the Phrenic nerve of the patient superimposed in a target rhythm not being synchronous with spontaneous breath of the patient, or prevention, delay or replacement of ventilation or reduction of high positive pressures during mechanical ventilation, wherein the repetition rate is, during night time, at every spontaneous breath of the patient, and, during day time, not operating the induction device, and wherein the induction device is operated to stimulate the Phrenic nerve of the patient superimposed in a target rhythm not being synchronous with spontaneous breath of the patient.

12. The method of claim 11, wherein the patient is ventilated.

13. The method of claim 11, wherein the induction device has an electro-magnetic field generator with a coil design to generate a spatial electro-magnetic field as the spatial field having the targeted shape, wherein the electro-magnetic field generator of the induction device is positioned at a human or animal patient, and wherein the induction device is operated to stimulate the Phrenic nerve of the patient by the spatial electro-magnetic field generated by the coil design.

14. The method of claim 11, wherein operating the induction device to stimulate the Phrenic nerve of the patient comprises operating the induction device for a stimulation duration matched to the specific treatment, comprising a step of defining the stimulation duration in accordance with the specific treatment.

15. The method of claim 11, wherein the specific treatment is reduction of risk of developing an acute respiratory distress syndrome or ventilator associated pneumonia or ventilator-induced lung injury, and the induction device is repeatedly operated in regular intervals throughout one day.

16. The method of claim 11, wherein the specific treatment is keeping or rebuilding function of the respiratory center which is connected to the phrenic nerve.

17. The method of claim 11, wherein the specific treatment is induction of breathing cycles or stimulation of deep breathing, comprising measuring an oxygen level or a carbon dioxide level in the blood of the patient, and operating the induction device when the measured oxygen level or carbon dioxide level bypasses a predefined threshold.

18. The method of claim 11, wherein a field intensity and a train duration of the induction device are adjusted such that:

the patient produces a tidal breath in a range of about 3 ml per kg body weight to about 6 ml per kg body weight, the patient produces a tidal breath in a range of about 6 ml per kg body weight to about 8 ml per kg body weight, the patient produces a tidal breath in a range of about 0 ml per kg body weight to about 3 ml per kg body weight, or the patient produces deep and strong breaths in a range of about 9 ml per kg body weight to about 15 ml per kg body weight.

19. A method of providing a specific treatment to a human or animal patient, comprising:

obtaining an induction device configured to generate a spatial field having a targeted shape;

positioning the induction device at a human or animal patient; and operating the induction device to stimulate a Phrenic nerve of the patient by the spatial field such that a diaphragm of the patient is activated, wherein operating the induction device comprises providing trains of the generated spatial field, wherein each train comprises an increase of an intensity of the spatial field ending at a target intensity of the spatial field.

* * * * *